(12) United States Patent
Walker et al.

(10) Patent No.: US 7,805,191 B2
(45) Date of Patent: Sep. 28, 2010

(54) CPR TIME INDICATOR FOR A DEFIBRILLATOR DATA MANAGEMENT SYSTEM

(75) Inventors: Robert G. Walker, Bothell, WA (US); Fred William Chapman, Newcastle, WA (US)

(73) Assignee: Physio-Control, Inc., Redmond, WA (US)

( * ) Notice: Subject to any disclaimer, the term of this patent is extended or adjusted under 35 U.S.C. 154(b) by 60 days.

(21) Appl. No.: 11/048,322

(22) Filed: Jan. 31, 2005

(65) Prior Publication Data

US 2006/0173500 A1 Aug. 3, 2006

(51) Int. Cl.
*A61N 1/39* (2006.01)

(52) U.S. Cl. .......................................................... 607/5
(58) Field of Classification Search .................... 607/5; 601/41–44
See application file for complete search history.

(56) References Cited

U.S. PATENT DOCUMENTS

| | | | | |
|---|---|---|---|---|
| 4,797,104 | A | * | 1/1989 | Laerdal et al. .............. 434/265 |
| 6,125,299 | A | | 9/2000 | Groenke et al. |
| 6,351,671 | B1 | * | 2/2002 | Myklebust et al. ............. 607/5 |
| 6,827,695 | B2 | | 12/2004 | Palazzolo et al. |
| 2002/0117173 | A1 | * | 8/2002 | Lynn et al. .............. 128/202.28 |
| 2003/0195775 | A1 | * | 10/2003 | Hampton et al. ................ 705/3 |
| 2004/0082888 | A1 | * | 4/2004 | Palazzolo et al. ............. 601/41 |
| 2004/0225238 | A1 | | 11/2004 | Sherman et al. |

FOREIGN PATENT DOCUMENTS

EP  1 057 451 A2  5/2000

OTHER PUBLICATIONS

Lars Wik, MD, PhD, Quality of Cardiopulmonary Resuscitation During Out-of Hospital Cardiac Arrest, (Reprinted) JAMA, Jan. 19, 2005-vol. 293, No. 3, pp. 299-304.
U.S. Appl. No. 11/272,177, filed Nov. 10, 2005, CPR Performance Reporting Systems.
Zoll Data Systems, "RescueNet Code Review, Getting Started Guide- Version 3.21", dated Aug. 25, 2005.
PCT International Search Report, Intl Appn. No. PCT/US2006/003424 (based on U.S. Appl, No. 11/418,322).
Office Action for U.S. Appl. No. 11/272,177, dated Dec. 9, 2009, (21 pgs.).

* cited by examiner

*Primary Examiner*—Eric D. Bertram
(74) *Attorney, Agent, or Firm*—Shumaker & Sieffert, P.A.

(57) ABSTRACT

A system is disclosed wherein patient data, such as an electrocardiogram ("ECG") signal or a chest impedance measurement signal, collected by a defibrillator device during a resuscitation event is analyzed and processed by a computing device to provide an assessment of CPR administered during the event. The CPR assessment results in one or more CPR figures of merit that relate to temporal characteristics of the CPR relative to the duration of the event. In one embodiment, the CPR figure of merit represents a percentage of the event period during which chest compressions were administered to the patient.

6 Claims, 5 Drawing Sheets

CPR TIME INDICATOR FOR A DEFIBRILLATOR DATA MANAGEMENT SYSTEM

TECHNICAL FIELD

The present invention relates generally to defibrillator systems. More particularly, the present invention relates to a data management system for a defibrillator system.

BACKGROUND

A normal human heart pumping pattern is called a sinus rhythm, and the pattern is regulated by the body's biological pacemaker within the upper right chamber of the heart, which is commonly referred to as the right atrium. This natural pacemaker, which is generally referred to as the sinoatrial ("SA") node, sends electrical signals to the right and left ventricular muscles in the lower chambers of the heart. The ventricular muscles then implement the pumping action under the control of the SA node. The right ventricular muscle pumps blood to the lungs for oxygenation, and the left ventricular muscle pumps the oxygenated blood to various parts of the body.

In certain circumstances, the normal or sinus heartbeat rhythm may be adversely affected as a result of some type of malfunction in the heart's electrical control system. When this type of malfunction occurs, an irregular heartbeat may result, causing the ventricular muscles to pump ineffectively, thus reducing the amount of blood pumped to the body. This irregular heartbeat is generally referred to as an arrhythmia.

A particularly serious arrhythmia is known as ventricular fibrillation ("VF"), which is a malfunction characterized by rapid, uncoordinated cardiac movements replacing the normal contractions of the ventricular muscles. In this event, the ventricular muscles are not able to pump blood out of the heart, and there is no initiation of a heartbeat. VF rarely terminates spontaneously, and is therefore a leading cause of sudden cardiac arrest. The unpredictability of VF and other irregular heart beat conditions exacerbates the problem, and emphasizes the need for early therapeutic intervention to prevent the loss of life.

Defibrillators are devices for providing life-saving electrical therapy to persons experiencing an irregular heat beat, such as VF. A defibrillator provides an electrical stimulus to the heart in an attempt to convert the irregular heat beat to a normal sinus rhythm. One commonly used type of defibrillator is the external defibrillator, which sends electrical pulses to the patient's heart through external electrodes applied to the patient's chest. External defibrillators may be manually operated (as are typically used in hospitals by medical personnel), semi-automatic, semi-automated, fully automatic, or fully automated devices, where they can be used in any location where an unanticipated need may occur.

In practice, defibrillation pulses are administered to the patient when necessary, and cardio-pulmonary resuscitation ("CPR") is administered between pulses. CPR includes the delivery of chest compressions to the patient (to stimulate blood flow) and the delivery of ventilations to the patient (to provide air to the lungs). Recent statistical studies suggest that the amount of time devoted to CPR during a typical resuscitation event may be less than optimal in real world situations. Although some of the defibrillator usage time is necessarily occupied by rhythm analysis and defibrillation functions—which in most cases preclude the simultaneous delivery of CPR—there may be an undesirable amount of "wasted" time during which neither the defibrillator device nor the caregiver are actively administering treatment to the patient.

Presently, there are no straightforward and elegant ways to assess the proportion of time that chest compressions and/or ventilations were performed during a resuscitation event. Such assessments can be useful during post-event review of a defibrillator usage case. Currently, caregivers or case reviewers must make educated guesses via laborious evaluation of ECG signal artifacts (which can be highly variable from case to case), captured scene audio (which may not be available for all defibrillator devices), device prompts, and expectations of caregiver behavior.

Accordingly, it is desirable to have a system for providing quantitative post-event feedback related to the amount and proportion of time that chest compressions and/or ventilations were performed during a cardiac arrest response treated by a defibrillator device. In addition, it is desirable to have a system for providing other figures of merit related to the delivery of CPR during a resuscitation event, where such figures of merit are determined from post-event patient data analysis. Furthermore, other desirable features and characteristics of the present invention will become apparent from the subsequent detailed description and the appended claims, taken in conjunction with the accompanying drawings and the foregoing technical field and background.

BRIEF SUMMARY

A system and method for assessing CPR performed during a resuscitation event processes patient data collected during the event for analysis in a post-event manner. The patient data, which can be an ECG signal and/or a patient impedance signal, is analyzed to determine temporal indicators related to a CPR figure of merit. The system is configured to generate a suitable report containing the CPR figure of merit for review and assessment of the treatment administered to the patient.

The above and other aspects of the invention may be carried out in one form by a method for assessing CPR performed during resuscitation therapy. The method involves obtaining an event time interval for a resuscitation event and processing post-event data for a patient to determine a temporal CPR percentage representing a percentage of the event time interval during which chest compressions were administered to the patient. The post-event data represents at least one patient signal electronically captured during the resuscitation event, such as an ECG signal or a patient impedance signal captured by a defibrillator device.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of practical defibrillator systems and that the system described herein is merely one exemplary application for the invention.

For the sake of brevity, conventional techniques related to ECG monitoring, patient impedance measurement, defibrillator device control, digital signal processing, data transmission, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

Figure 1:
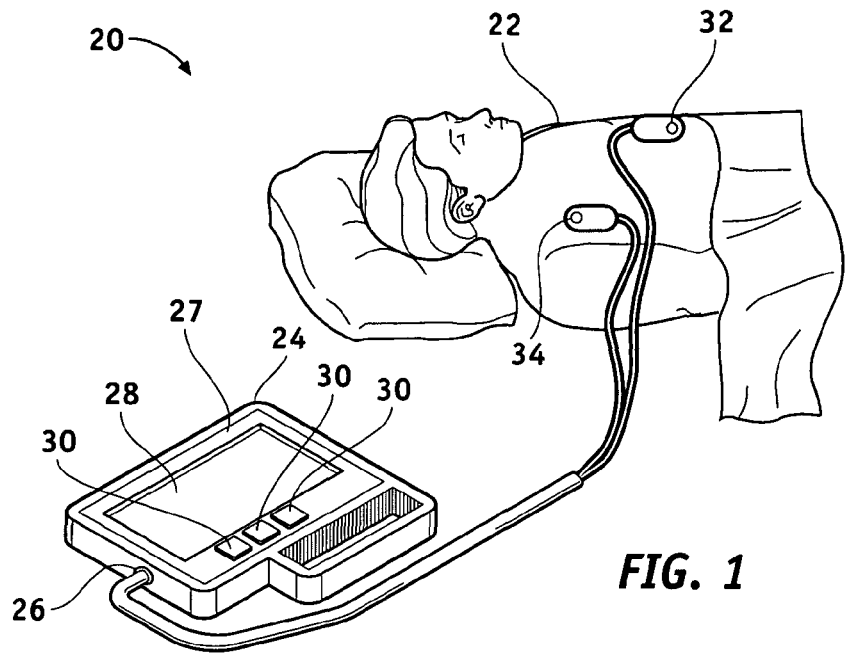
FIG. 1 is an illustration of an external defibrillator system connected to a patient.

FIG. 1 depicts a defibrillator system 20 that is configured to deliver defibrillation therapy to a patient 22, such as a victim of VF. The defibrillator system 20 includes, but is not limited to, an external defibrillator device 24 having a connection port 26 that is configured to receive one or more cables or wires corresponding to one or more patient electrodes 32/34. In practice, external defibrillator device 24 can be any number of external defibrillators, such as an automatic external defibrillator or an automated external defibrillator, a semi-automatic or semi-automated external defibrillator, or a manually operated external defibrillator. Fully- or semi-automated or automatic defibrillators are sometimes referred to as "AEDs."

External defibrillator device 24 preferably includes a user interface 27 having a display 28 that is configured to visually present various measured or calculated parameters of patient 22 and/or other information to the operator (not shown) of external defibrillator device 24. For example, display 28 can be configured to visually present the transthoracic impedance, ECG, and/or other physiology signals of patient 22. User interface 27 can also include one or more input devices (e.g., switches or buttons) 30 that are configured to receive commands or information from the operator. External defibrillator device 24 is configured to generate a charge that is delivered to patient 22 as the defibrillation therapy pulse via electrodes 32/34.

Electrodes 32/34 are typically multifunction electrodes in that they are configured both to provide defibrillation therapy and to sense one or more physiology and/or physical parameters of patient 22 that are received by external defibrillator device 24 at connection port 26. This is a typical configuration in an AED type device; it will be understood by those skilled in the art that electrodes may be designed differently for different machines. Other defibrillators, including for example manual defibrillators, may also have an additional set of electrodes (not shown), in addition to the multifunction electrodes, used to receive ECG information. These additional electrodes, ECG electrodes, are generally smaller than therapeutic/multifunction electrodes, and ECG electrodes typically plug into a separate port (not shown) than the therapeutic/multifunction electrodes. As is understood in the art, ECG electrodes typically have a three wire lead, though other arrangements are possible. The signals provided by the one or more electrodes 32/34 are preferably evaluated by external defibrillator device 24 to determine, among other things, whether a defibrillation shock should be applied to patient 22 in accordance with techniques known to those of ordinary skill in the art. This external defibrillator device 24 can, in some embodiments, also evaluate the signals provided by the one or more electrodes 32/34 to determine the waveform parameters of the defibrillation shock (e.g., sinusoidal, monophasic, biphasic, truncated) as well as magnitude and duration; AEDs often include a preprogrammed energy protocol. As is understood in the art, manual defibrillators may allow for a manual selection of shock parameters.

Figure 2:
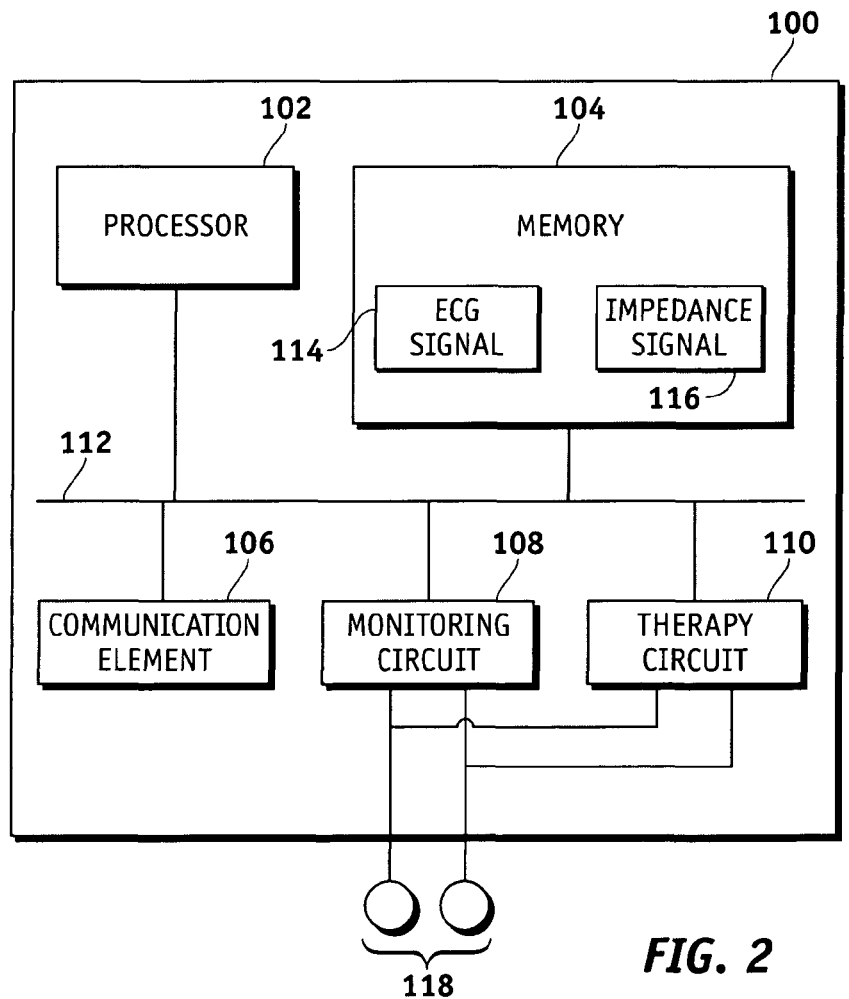
FIG. 2 is a schematic representation of an external defibrillator system configured in accordance with the invention.

FIG. 2 is a schematic representation of a defibrillator 100 suitable for use with the invention as further described herein. Although not shown in FIG. 2, defibrillator 100 may include a number of functional elements, logical elements, and/or hardware components that support conventional defibrillator features unrelated to the invention. Defibrillator 100 generally includes a processor 102, a suitable amount of memory 104, a data communication element 106, a monitoring circuit 108, and a defibrillation therapy circuit 110. Defibrillator 100 may include a data bus 112 to facilitate communication of data or control signals between some or all of the above components.

Processor 102 may be any general purpose microprocessor, controller, or microcontroller that is suitably configured to control the operation of defibrillator 100. Memory 104 may be realized as any processor-readable medium, including an electronic circuit, a semiconductor memory device, a ROM, a flash memory, an erasable ROM, a floppy diskette, a CD-ROM, an optical disk, a hard disk, an organic memory element, or the like. As described in more detail below, memory 104 is capable of storing patient data captured during a resuscitation event, e.g., ECG signals 114, patient impedance signals 116, or the like.

Communication element 106 is configured to communicate with a remote computing device (described below). In particular, communication element 106 is suitably configured to communicate post-event patient data to the remote computing device in accordance with at least one data communication protocol. As used herein, "post-event patient data" and "post-event data" refers to data that is transferred, analyzed, reported, or otherwise processed after a resuscitation event (except in the case of real-time handling of patient data as described in more detail below). Thus, although defibrillator 100 obtains patient data during the resuscitation event, post-event patient data can be stored by defibrillator 100 for post-event transfer, analysis, and processing. For example, post-event data may include a patient impedance signal, a patient ECG signal, and/or data recorded, collected, or generated by defibrillator 100 during an event, including, without limitation, defibrillation pulse delivery times, voice prompt times, and rhythm analysis times.

In the example embodiment, communication element 106 communicates with the remote computing device in accordance with at least one standardized data communication protocol (either wireless or wired). Such standardized data communication protocols include, without limitation: Bluetooth; IEEE 802.11 (any variation thereof); Ethernet; IEEE 1394 (Firewire); GPRS; USB; IEEE 802.15.4 (ZigBee); or IrDA (infrared). Communication element 106 may be realized with hardware, software, and/or firmware using known techniques and technologies. For example, defibrillator device 100 may include a wireless port configured to support wireless data communication with the remote computing device and/or a cable or wire port configured to support data communication, via a tangible link, with the remote computing device. In this regard, communication element 106 and any corresponding logical or software elements, individually or in combination, are example means for providing the post-event patient data to the remote computing device.

Alternatively (or additionally), the post-event data may be transferred to the remote computing device using portable storage media. For example, the post-event data can be transferred or copied from memory 104 onto a portable storage device for transport to the remote computing device. The portable storage media may include, without limitation, a magnetic disk, a semiconductor memory device, a flash memory device, a floppy diskette, an optical disk (e.g., a CD or a DVD), a hard disk, or the like.

Alternatively (or additionally), the post-event data may be transferred, via communication element 106 or using portable storage media as described above, from defibrillator 100 to another medical device such as a second defibrillator. For example, where a first responder (for example, a police officer, firefighter or bystander) has used an AED to treat a patient, it is desirable to transfer data stored on the AED concerning that rescue event (including patient physiological data and information on therapies applied to the patient) to a defibrillator or other medical device used by medical personnel (for example, emergency medical technicians) who take over care of the patient. This transferred data may later be subsequently transferred from the medical device to still another medical device or to a computing device. The post-event data from defibrillator 100 may be merged with other data from the medical device for transfer to yet another medical device or computing device.

In operation, defibrillator 100 communicates with patient sensors that may be applied to or attached to the patient undergoing treatment. In a practical embodiment, patient sensors may be realized as conventional defibrillation therapy electrode patches 118 that are capable of monitoring patient data and delivering defibrillation pulses to the patient. For example, electrode patches 118 are preferably configured to detect the patient's ECG signal and the patient's chest impedance using techniques known to those skilled in the art (chest impedance is typically measured by applying a high frequency variable level carrier wave into the patient via electrode patches 118). In a practical embodiment, defibrillator 100 can concurrently sample the ECG and chest impedance signals during a resuscitation event. Although only two patient sensors are depicted in FIG. 2, a practical embodiment may employ any number of patient sensors defining any number of ECG leads, any number of patient sensors defining any number of chest impedance measurement circuits, and any number of patient sensors configured to monitor, sense, or detect other patient related data or signals that may be utilized to assess the quality of CPR as further described herein. For example, patient sensors may include one or more pressure sensors, one or more accelerometers, or any number of sensors, transducers, or detectors that indicate characteristics of CPR such as, for example, rate of compression delivery, duty cycle of compression delivery, depth of compressions, or force of compression delivery.

Therapy circuit 110 is generally responsible for the application of defibrillation pulses to the patient. In an automated or automatic defibrillator, therapy circuit 110 may determine whether a defibrillation pulse is warranted and, if so, charge and discharge the defibrillation pulse circuit as needed. Therapy circuit 110 preferably operates in accordance with known techniques and methodologies and, therefore, will not be described in detail herein.

Monitoring circuit 108 is suitably configured to receive the patient data or signals from patient sensors 118. As described above, such data may represent the patient ECG signal and/or the patient chest impedance signal. Monitoring circuit 108 may process the received data into a format for storage in memory 104, into a format for interpretation or further analysis by defibrillator 100 (therapy circuit 110 in particular), into a format compliant with a data communication protocol to facilitate transfer to a remote computing device, and/or into any suitable format. In practice, monitoring circuit 108 may perform analog to digital conversion on the received signals or otherwise condition the received signals for subsequent handling by defibrillator 100. In one preferred embodiment that handles post-event data, monitoring circuit 108 facilitates storage of data representing the patient ECG signal 114 and storage of data representing the patient chest impedance signal 116. In this context, the stored post-event data represents at least one patient signal electronically captured during the resuscitation event. The storage of such post-event data enables subsequent review and analysis of the resuscitation event.

Figure 3:
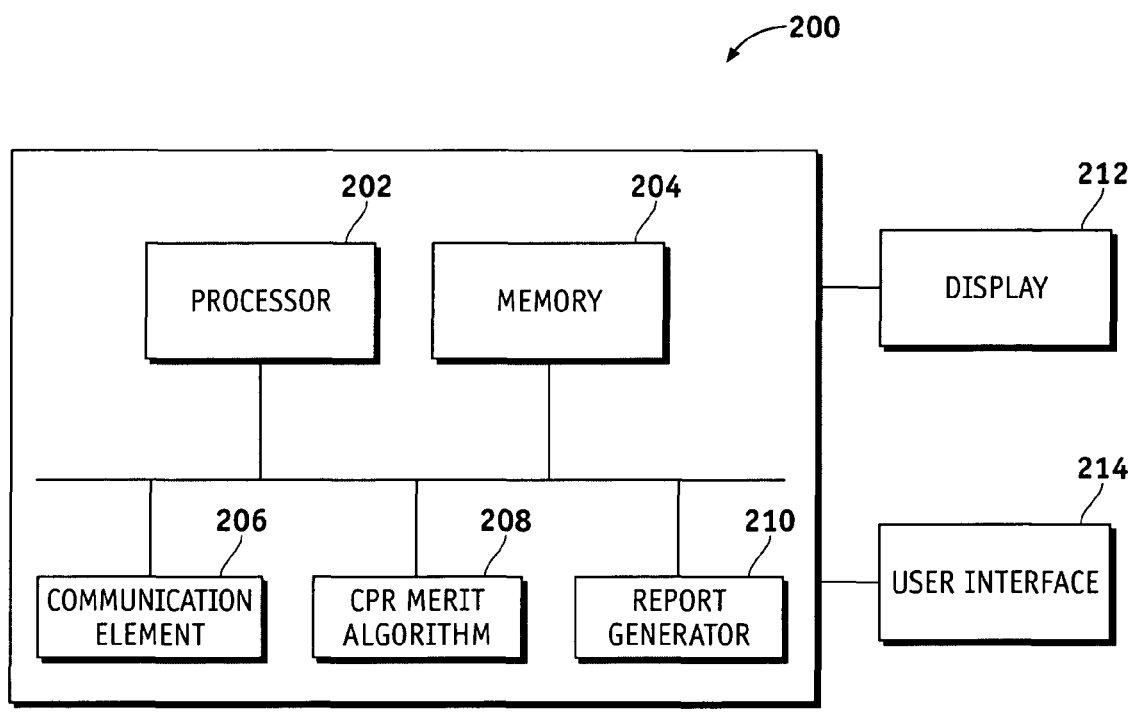
FIG. 3 is a schematic representation of a computing device configured in accordance with the invention.

FIG. 3 is a schematic representation of a computing device 200 configured in accordance with the invention. Computing device 200 may be any known device or system configured to support the CPR assessment techniques described herein, including, without limitation: a standard desktop personal computer, a portable computer such as a laptop computer or a tablet computer, a personal digital assistant ("PDA"), a suitably configured mobile telephone, or the like. Computing device 200 generally includes a processor 202, an appropriate amount of memory 204, a data communication element 206, logic corresponding to a CPR merit algorithm 208, a report generator 210, a display element 212, and a user interface 214.

As with most commercially available general purpose computing devices, a practical computing device 200 may be configured to run on any suitable operating system such as Unix, Linux, the Apple Macintosh OS, any variant of Microsoft Windows, a commercially available real time operating system, or a customized operating system, and it may employ any number of processors 202, e.g., the Pentium family of processors by Intel, the processor devices commercially available from Advanced Micro Devices, IBM, Sun Microsystems, or Motorola, or other commercially available embedded microprocessors or microcontrollers.

The logical and functional elements of computing device 200 may communicate with system memory (e.g., a suitable amount of random access memory), and an appropriate amount of storage or "permanent" memory. For computing device 200, memory 204 may represent such random access memory and/or such permanent memory. The permanent memory may include one or more hard disks, floppy disks, CD-ROM, DVD-ROM, magnetic tape, removable media, solid state memory devices, or combinations thereof. In accordance with known techniques, operating system and application programs reside in the permanent memory and portions thereof may be loaded into the system memory during operation. In accordance with the practices of persons skilled in the art of computer programming, the invention is described herein with reference to symbolic representations of operations that may be performed by the various computing components or devices. Such operations are sometimes referred to as being computer-executed, computerized, software-implemented, or computer-implemented. It will be appreciated that operations that are symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the systems described herein (which may reside at defibrillator 100 or computing device 200) are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

The specific configuration, operating characteristics, and functionality of display element 212 and user interface 214 can vary depending upon the practical implementation of computing device 200. For example, if computing device 200 is a desktop computer, then display element 212 may be a CRT, LCD, or plasma monitor, and user interface 214 may include a keyboard and a pointing device such as a mouse or touchpad (user interface 214 may also include a speaker system, a microphone system, a camera system, or the like). Alternatively, if computing device 200 is a PDA, then display element 212 may be a small scale LCD integrated into the PDA itself, and user interface 214 may include a small scale keypad, a stylus writing screen, a touchpad, or the like.

Computing device 200 may be configured to support data communication with defibrillator 100. Such data communication may be carried out over any number of wireless data communication links and/or any number of wired data communication links. Alternatively, computing device 200 may obtain post-event data from defibrillator 100 via a portable storage device. To facilitate such data communication, computing device may include data communication element 206. In particular, communication element 206 may be suitably configured to receive post-event patient data (captured by defibrillator 100) in accordance with at least one data communication protocol as described above in connection with data communication element 106. Furthermore, communication element 206 and computing device 200 may be configured for compatibility with a particular data file format used by the defibrillator. For example, communication element 206 and computing device 200 may be configured to support different patient data file formats that may be used by different manufacturers of defibrillator devices. Communication element 206 may be realized with hardware, software, and/or firmware using known techniques and technologies. Communication element 206 and any corresponding logical or software elements, individually or in combination, are example means for receiving post-event patient data from a remote defibrillator device such as defibrillator 100.

Computing device 200 is configured to assess the CPR administered during a resuscitation event after completion of the event. In this regard, computing device 200 may include a logical, program, or processing element corresponding to CPR merit algorithm 208. In a practical embodiment, CPR merit algorithm 208 may be realized as a software program maintained in memory 204 and performed by processor 202. For example, CPR merit algorithm 208 and one or more associated application programs may be embodied in a medical informatics software system such as the CODE-STAT™ product from Medtronic, Inc. Briefly, CPR merit algorithm 208 analyzes the post-event patient data (e.g., the patient ECG signal and/or the patient chest impedance signal obtained from defibrillator 100) and generates one or more figures of merit that describe the CPR administered during the resuscitation event. Although the following description focuses on figures of merit related to the application of chest compressions, the invention also contemplates figures of merit related to the application of ventilations. The figures of merit may be alphanumeric values, graphs, charts, scores, or the like. In a practical embodiment, report generator 210 formats and generates one or more reports for review by a user of computing device 200. The report may be displayed on display element 212, printed, rendered in a format suitable for facsimile or email transmission, rendered in an audible format, or otherwise generated for communication to the user. In practice, a report may include, without limitation: patient identification data; event or incident identification data; a graphical representation that summarizes the distribution of various activities during the resuscitation event (such as CPR, application of defibrillation therapy pulses, or the like); interval statistics (such as a ratio or percentage of time devoted to chest compressions and/or ventilations, an average rate of compressions/ventilations, an effective rate of compressions/ventilations, and the average duty cycle of compressions/ventilations); and overall statistics (such as the total duration of defibrillator device use, the total duration of CPR, the total duration of compressions/ventilations, the number of analyses performed, the number of pulse checks performed, the number of defibrillation pulses applied, the number and duration of "hands-off" pauses, and the like).

Figure 4:
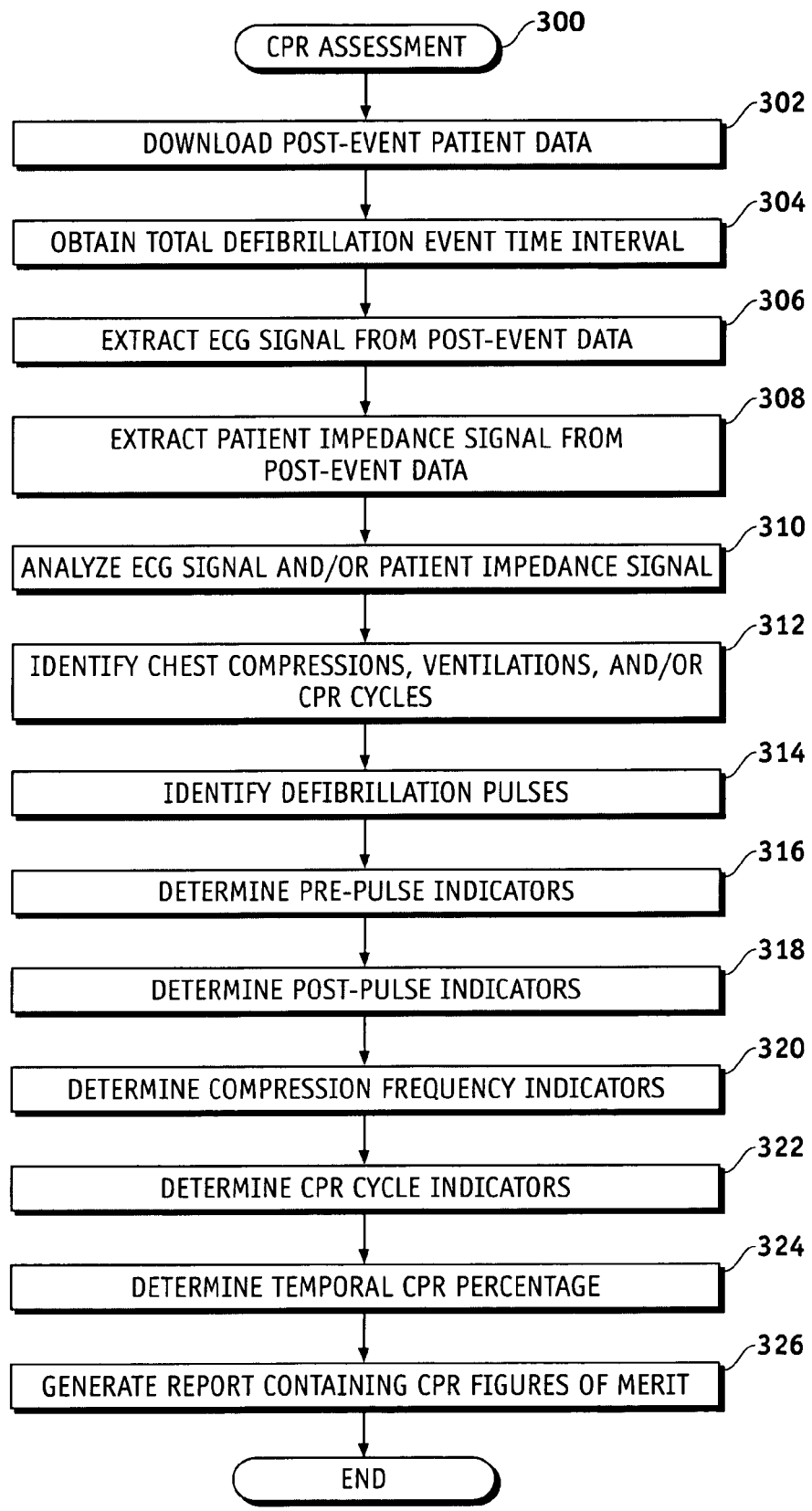
FIG. 4 is a flow diagram of a CPR assessment process according to the invention.

FIG. 4 is a flow diagram of a CPR assessment process 300 according to the invention. Process 300 may be performed by a computing system, such as computing device 200, following a resuscitation event. Process 300 assumes that patient data has been captured (and possibly stored) by a defibrillator, such as defibrillator 100. The various tasks performed in connection with process 300 may be performed by software, hardware, firmware, or any combination thereof. For illustrative purposes, the following description of process 300 may refer to elements mentioned above in connection with FIGS. 1-3. In practical embodiments, portions of process 300 may be performed by different elements of the remote computing system. It should be appreciated that process 300 may include any number of additional or alternative tasks, the tasks shown in FIG. 4 need not be performed in the illustrated order, and process 300 may be incorporated into a more comprehensive procedure or process having additional functionality not described in detail herein.

CPR assessment process 300 begins by downloading post-event patient data to the computing device (task 302). Alternatively, process 300 may begin by transferring post-event patient data from portable storage media to the computing device. During task 302, the computing device receives the post-event data from a remote defibrillator device. The post-event data represents at least one patient signal that was electronically captured during a resuscitation event. For example, the post-event data may represent the patient ECG signal and/or the patient chest impedance signal captured during a given resuscitation event. Post-event data may also include device events or actions (for example, rhythm analyses, voice prompts, or defibrillation pulses) that are marked or annotated by the device at the appropriate location in the ECG and/or impedance signals. In the preferred embodiment, the computing device processes at least the chest impedance signal captured by the defibrillator. Task 302 (or its equivalent) may be performed at any time after the resuscitation event has ended.

Figure 5:
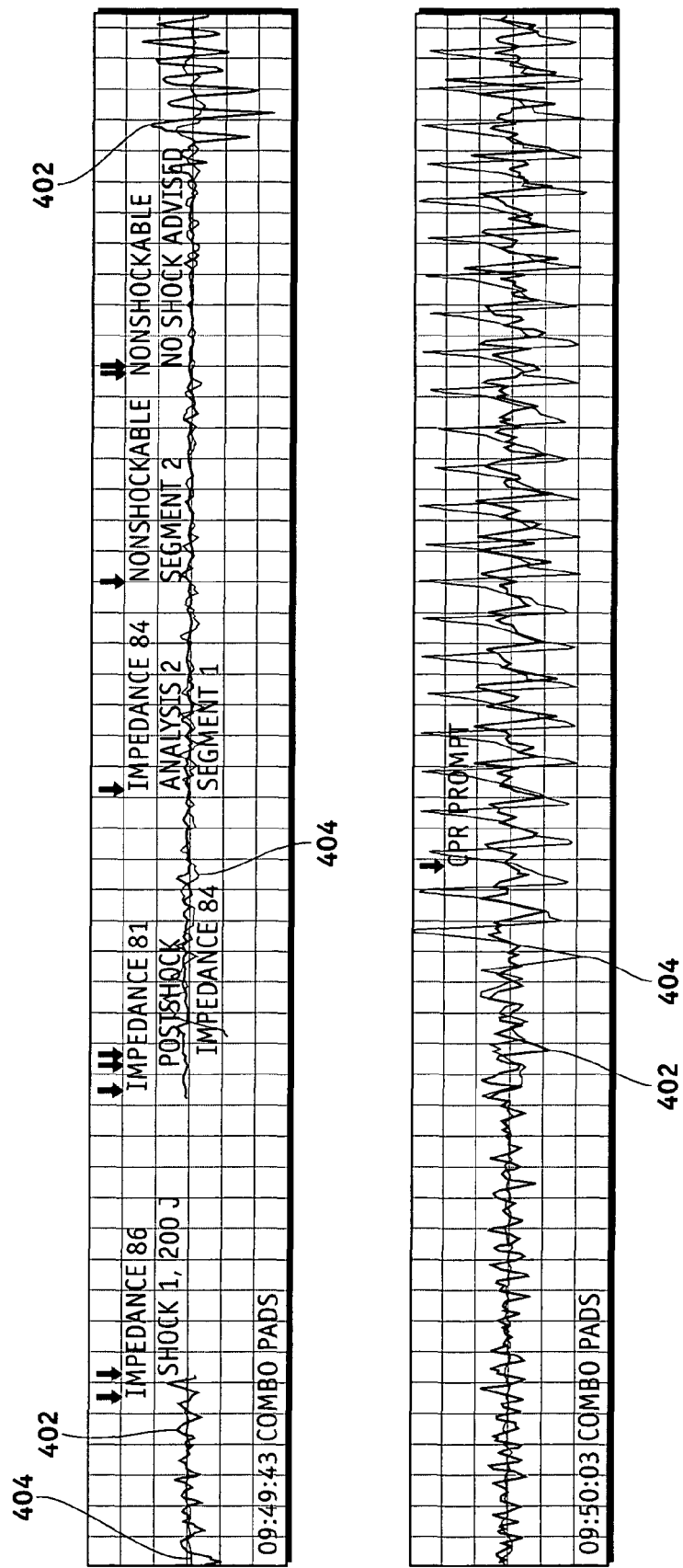
FIGS. 5 and 6 are example graphs of patient data signals captured by a defibrillator device during a resuscitation event.

FIG. 5 is a graphical representation of an example patient ECG signal 402 and an example patient chest impedance signal 404 corresponding to a resuscitation segment during which the patient experiences VF, a defibrillation therapy pulse is administered to the patient, and then CPR is administered to the patient. The lower graph in FIG. 5 represents a continuation of the upper graph in FIG. 5. These example signals are provided to aid in the description of CPR assessment process 300 and are not intended to limit the scope of the invention in any way. The graphical representation depicted in FIG. 5 may be generated by a defibrillator device for display at the device, at an evaluation computer system, and/or for storage as post-event data. In FIG. 5, the displayed text items are annotations generated by the defibrillator device at specific times during the resuscitation event. Thus, for example, the instant of the defibrillation pulse is indicated by the text "Shock 1, 200 J," and a downward pointing arrow above that text at the instant that the ECG signal stops (defibrillation pulse delivery causes the ECG display to go blank for a few seconds). Similarly, the post-therapy rhythm analysis time and outcome is automatically annotated by the defibrillator device (indicated by the text "Segment 1," "Segment 2," and "Nonshockable"), as is a subsequent voice prompt to begin CPR (indicated by the text "CPR Prompt"). The large spikes in the patient chest impedance signal 404 that begin immediately preceding the "CPR Prompt" annotation represent chest compressions. In this regard, a system according to one example embodiment of the invention identifies each of the compression spikes, and then calculates all of the various measures and metrics described herein. For example, the time point of the defibrillation pulse and the time point of the first compression of that sequence can be used to derive a "post-defibrillation pause" figure of merit.

Figure 6:
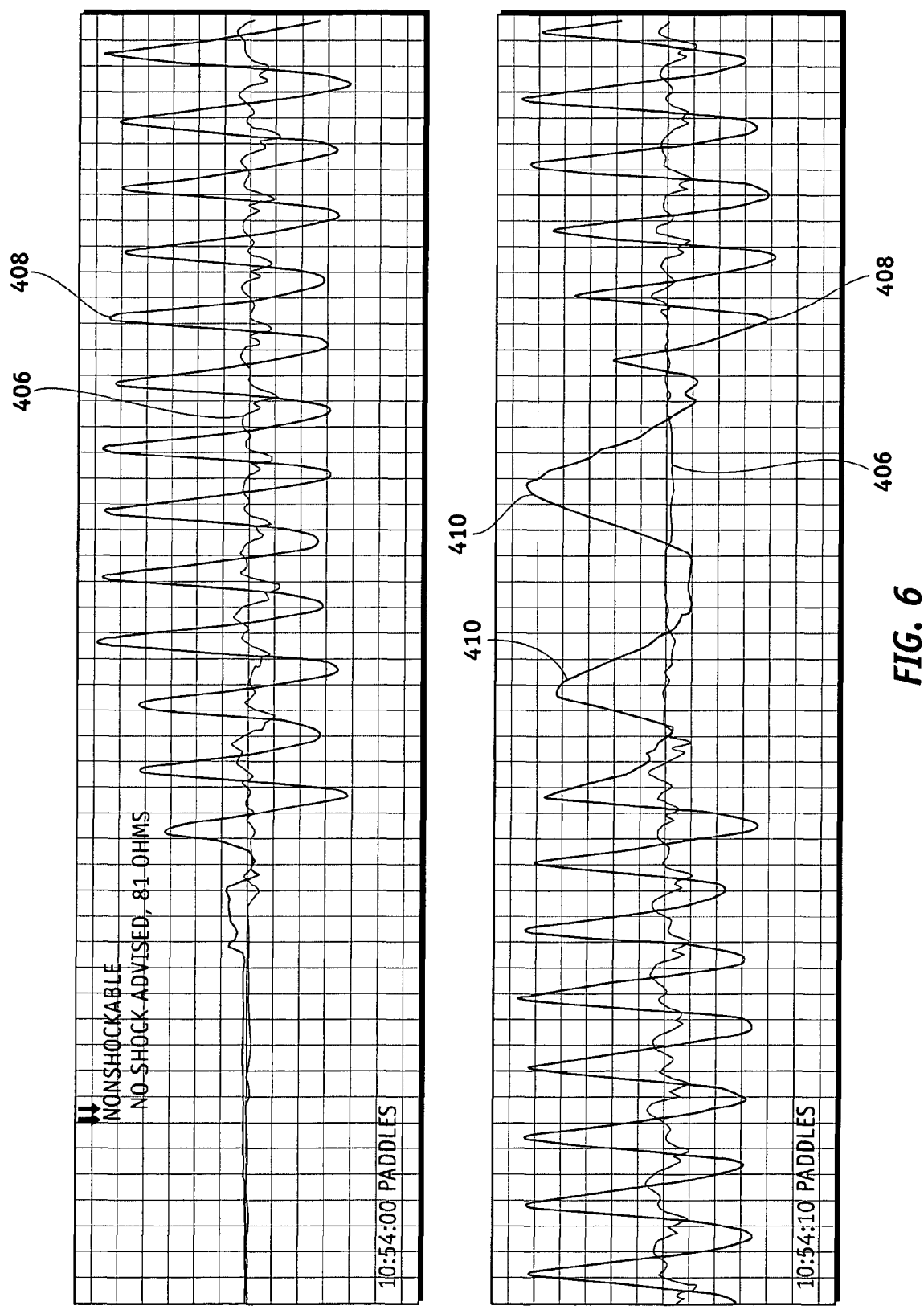

FIG. 6 is a graphical representation of an example patient ECG signal 406 and an example patient chest impedance signal 408 corresponding to a resuscitation segment during which chest compressions interspersed with ventilations are administered to the patient. The lower graph in FIG. 6 represents a continuation of the upper graph in FIG. 6. These example signals are provided to aid in the description of CPR assessment process 300 and are not intended to limit the scope of the invention in any way. The graphical representation depicted in FIG. 6 may be generated by a defibrillator device for display at the device, at an evaluation computer system, and/or for storage as post-event data. A normal ECG signal conveys a regular wave of heartbeats, however, during VF, the ECG signal is erratic or flat. The chest impedance signal is usually characterized by relatively broader peaks and valleys that indicate ventilations and relatively narrower peaks and valleys that indicate chest compressions. In FIG. 6, the narrow pulses of patient chest impedance signal 408 represent compressions, while the two broader pulses (identified by reference number 410) represent ventilations. Typical chest compression rates during CPR would range from 60 to 120 compressions per minute, with recommended rates of 80 to 100 compressions per minute. Typical ventilation rates would range from 6 to 35 per minute, with recommended rates nearer the lower end of that range. A typical resuscitation event will include an interval of CPR delivered in sequences of 15 compressions interspersed by two ventilations, followed by an interval of analysis of the ECG to determine whether delivery of a defibrillating pulse is advisable, and then possibly by one or more defibrillation pulses, if the analysis recommends defibrillation. A five-to-one ratio may also be part of CPR teaching; that is, some settings and providers will pause every five compressions to deliver one breath. The process of CPR, followed by ECG analysis, followed by defibrillation therapy, may be repeated in whole or in part during the resuscitation event. A system according to an example embodiment of the invention may identify the compression spikes and/or the ventilation spikes for purposes of calculating one or more figures of merit for the resuscitation event.

Referring again to FIG. 4, CPR assessment process 300 also obtains an event time interval for the resuscitation event (task 304). The event time interval may be any period of time spanning any portion of the resuscitation event. In one preferred embodiment, task 304 obtains the total duration of the resuscitation event, which may be represented by the time period defined by the start and end of the patient ECG signal. Alternatively, the total time may be defined as the time period from when the patient is first detected by the defibrillator to the time when the defibrillator is turned off (or when the patient sensors are removed from the patient). In practice, the event time interval obtained during task 304 can be derived from the post-event data, or it may be a parameter generated by the defibrillator for use by the computing device. For example, the computing device may be configured to analyze the post-event data to determine the duration of the event. It should be appreciated that CPR merit algorithm 208, processor 202, and any corresponding logical or software elements, individually or in combination, are example means for obtaining the event time interval.

Depending upon the format of the post-event data received from the defibrillator, it may be necessary for the computing device to extract or otherwise resolve the patient ECG signal from the post-event data (task 306) and extract or otherwise resolve the patient chest impedance signal from the post-event data (task 308). These tasks may be performed to facilitate efficient analysis and interpretation of the respective patient signals by CPR merit algorithm 208 as explained below.

Generally, CPR assessment process 300 processes and analyzes certain characteristics of the post-event data (e.g., the ECG signal and/or the patient impedance signal) to identify qualities and features of the CPR chest compressions or CPR ventilations administered to the patient during the resuscitation event (task 310). The manner in which the post-event data is examined may vary depending upon the desired figure of merit or the specific type of post-event data under consideration. For example, in one embodiment, the post-event data is analyzed to identify periods during which chest compressions were administered to the patient (task 312). As shown in FIG. 5, chest compressions are typically administered in multiples during a given CPR cycle. For example, a CPR protocol may call for 100 chest compressions during a 60 second cycle. Task 312 may identify the start time of each cycle, the end time of each cycle, the number of chest compressions actually delivered during the cycle, the rate of chest compression delivery during the cycle, the length of pauses between chest compressions within a cycle, the duration of each chest compression, the duty cycle of the chest compressions, or the like. In a practical embodiment, task 312 may identify periods during which ventilations were administered to the patient. In this regard, task 312 may identify the number of ventilations administered to the patient, the rate at which ventilations were administered to the patient, the duration of each ventilation, or the like. In accordance with one practical embodiment, task 312 may be performed by CPR merit algorithm 208 by analyzing fluctuations in the patient ECG signal, fluctuations in the patient chest impedance signal, and/or other temporal artifacts in the post-event data to identify, characterize, or quantify the chest compressions and/or ventilations administered during the event. In this regard, CPR merit algorithm 208, processor 202, and any corresponding logical or software elements, individually or in combination, are example means for processing/analyzing the post-event data.

CPR assessment process 300 may also analyze characteristics of the post-event data, such as event markers or annotations automatically generated by the defibrillator device and inserted into the post-event data, to identify times during the resuscitation event when the defibrillator device took certain actions, such as analyzing the patient's heart rhythm, administering defibrillation pulses to the patient, or providing voice prompts to the rescuer (task 314). Following task 314, the computing device can statistically recreate the resuscitation event, including the timing of chest compressions and ventilations, as well as the timing of rhythm analyses, defibrillation pulses, and voice prompts. Generally, CPR assessment process 300 derives at least one CPR figure of merit from the post-event data, where the CPR figure of merit is indicative of temporal characteristics of chest compressions administered to the patient and/or temporal characteristics of ventilations administered to the patient, relative to the timing of some aspect of the resuscitation event. Example CPR figures of merit are described in detail below.

One example CPR figure of merit relates to the amount of time between a final chest compression of a CPR cycle and the application of the next defibrillation pulse. As used herein, this figure of merit refers to a pre-defibrillation pause indicator that represents the period between a defibrillation pulse and a final chest compression administered to the patient prior to that defibrillation pulse. In this regard, CPR assessment process 300 may determine one or more pre-defibrillation pause indicators for the given resuscitation event (task 316). In practice, CPR merit algorithm 208 can determine this period by identifying the last compression in a cycle, marking the time of that compression, identifying the next defibrillation pulse, and marking the time of that pulse. In some cases, a lengthy pause between chest compressions and a defibrillation pulse is undesirable and, therefore, a pre-defibrillation pause indicator of such a lengthy pause will adversely affect the CPR figure of merit.

Another example CPR figure of merit relates to the amount of time between a defibrillation pulse and the next chest compression. As used herein, this figure of merit refers to a post-defibrillation pause indicator that represents the period between a defibrillation pulse and an initial chest compression administered to the patient subsequent to that defibrillation pulse. In this regard, process 300 may determine one or more post-defibrillation pause indicators for the given resuscitation event (task 318). In practice, CPR merit algorithm 208 can determine this period by identifying a defibrillation pulse, marking the time of that pulse, identifying the next chest compression, and marking the time of that compression. As mentioned above, in some cases, a lengthy pause between a defibrillation pulse and the next chest compression is undesirable. In such cases, a post-defibrillation pause indicator of a lengthy pause will adversely affect the CPR figure of merit.

Another example CPR figure of merit relates to the frequency of chest compressions administered during a given compression cycle. As used herein, this figure of merit refers to a compression frequency indicator that represents a period between individual chest compressions in a given cycle. To this end, CPR assessment process 300 may determine one or more compression frequency indicators for the given event (task 320). In a practical embodiment, CPR merit algorithm 208 can determine this frequency by identifying a CPR compression cycle, counting the number of chest compressions administered during that cycle, and marking the time of each compression. Thereafter, CPR merit algorithm 208 can generate an approximate compression frequency (in compressions per unit of time) corresponding to the given CPR cycle. Depending upon the specific CPR protocol, the compression frequency indicator will adversely affect the CPR figure of merit if it significantly departs from the ideal compression frequency called for by that CPR protocol.

Yet another example CPR figure of merit relates to the timing of CPR compression cycles administered during a given resuscitation event. As used herein, this figure of merit refers to a CPR cycle indicator that represents a period between adjacent CPR compression cycles. Thus, CPR assessment process 300 may determine one or more CPR cycle indicators for the given event (task 322). In a practical embodiment, CPR merit algorithm 208 can determine this indicator by identifying the CPR compression cycles, marking the start time and end time for each cycle, and calculating the time period between any two adjacent cycles. In some cases, a lengthy pause between chest compression cycles is undesirable. In such cases, a CPR cycle indicator of a lengthy pause will adversely affect the CPR figure of merit. An alternative way of looking at this would be to use the identified timing of compressions to calculate the rate, and then to compare the calculated rate to desired compression rates, which nominally would be 80-100 compressions per minute. Rates above or below the desired rates should be discouraged (and the figure of merit would reflect that).

An additional CPR figure of merit relates to the relative amount of time spent administering chest compressions during the resuscitation event. As used herein, this figure of merit refers to a temporal CPR percentage that represents a percentage of an event time interval (e.g., the total event time) during which chest compressions were administered to the patient. In this regard, CPR assessment process 300 may determine the temporal CPR percentage for the given event (task 324). In a practical embodiment, CPR merit algorithm 208 can determine the temporal CPR percentage by identifying the CPR compression cycles, marking the start time and end time for each cycle, calculating the total amount of time spent administering chest compression cycles, and identifying the total event time. Thereafter, the temporal CPR percentage may be determined by expressing the total combined chest compression time as a percentage of the total event time. Typically, a low temporal CPR percentage is undesirable because it indicates less time spent performing chest compressions. In contrast, a high temporal CPR percentage is usually desirable because it indicates more time spent performing chest compressions. Consequently, a low percentage will adversely affect the CPR figure of merit.

Yet another CPR figure of merit relates to the percentage of recommended "hands on time" during which the caregiver was actually administering compressions. For example, in an AED application, the data from the defibrillator device may include markings indicating when voice prompts were given. The AEDs instruct the rescuer not to touch the patient during some intervals, e.g., intervals during which the AED is analyzing the ECG or delivering a defibrillation shock. Thus, there may be periods of time during the resuscitation event when the rescuer should not be administering compressions. In this regard, it is possible in post-event review to know exactly how much of the time the AED was "asking for" CPR to be delivered (referred to in this context as "hands on time"). This figure of merit could be used to grade the compressions administered during the recommended hands on time.

The system may also generate one or more figures of merit related to ventilations administered to the patient. For ventilation, one important aspect is to ensure that ventilations are not provided at too high a rate, because excessive ventilation rates can adversely affect the hemodynamics of CPR (for example, it is generally accepted that a rate above approximately 20 ventilations per minute is undesirable). In other words, it is generally thought to be a good idea to deliver some breaths, but important not to overdo the ventilations. Accordingly, a suitable figure of merit is responsive to a ventilation rate based upon the number of ventilations administered to the patient during a given event time interval, where calculated ventilation rates that fall above or below a target rate adversely affect the figure of merit.

CPR assessment process 300 may generate a report (or any number of reports) containing one or more CPR figures of merit as described above (task 326). The report may be rendered on display element 212, printed, generated in an audible format, or transmitted via facsimile or email. Of course, in a network environment, the report may be rendered on or transmitted to any number of computing devices that are in communication with the remote computing device responsible for the actual processing and analysis. A simple, quantitative report that indicates the proportion or percentage of defibrillator use time occupied by chest compressions can be useful for a number of practical reasons, including, without limitation: emergency medical services recordkeeping; caregiver training; development of new resuscitation protocols; controlling for certain parameters in clinical research reports or evaluations; and legal verification that appropriate CPR was administered to the patient. Although not shown in FIG. 4, process 300 may be performed for multiple cases and may include additional tasks associated with the collection and processing of multiple case data, which can be utilized to generate statistical averages and/or trending data.

One refinement of CPR assessment process 300 would be to calculate the CPR figure of merit for the portion of the event that occurs before the return of spontaneous circulation (rather than for the entire event). This would appropriately avoid "penalizing" the figure of merit when the caregiver has properly stopped CPR once a pulse returns. The assessment of when a pulse or spontaneous circulation returns could be made and manually entered by a reviewer, making use of audio recordings from the scene, from separate records of the time course of the resuscitation, or the like. Alternatively, the assessment of spontaneous circulation could be determined automatically from a system that has a pulse detection capability, using technology designed to detect a pulse based on any of several candidate physiologic measurements.

The results obtained by CPR assessment process 300 may be useful in combination with the results obtained from other algorithms such as algorithms that analyze characteristics of the ventricular fibrillation signal to estimate the state or viability of the patient's heart. For example, trend information about the characteristics of the ventricular fibrillation signal in combination with information about CPR performance over some time interval during a resuscitation event might provide insight into the effectiveness of the CPR provided to the patient, or the duration or conditions of the cardiac arrest.

The functionality of computing device 200 may also be incorporated into defibrillator device 100, thus allowing real-time or approximately real-time analysis and assessment of CPR. Results of the analysis could be displayed, printed, or generated in audible form by defibrillator device 100. Results of the analysis performed in real-time or approximately real-time could also be used to have defibrillator device 100 provide feedback to a caregiver who is in the process of providing CPR, in the form of visual or aural prompts which provide CPR information, guidance, or encouragement to the caregiver. For example, if the analysis shows that compressions are not being given at an appropriate frequency, aural voiced prompts could instruct the caregiver to speed up or to slow down the compression rate. As another example, if the analysis shows that CPR is being performed in an appropriate manner, a prompt can inform the caregiver and provide encouragement to continue the effort (e.g., "Good job; keep going"). In such an embodiment, the patient related data need not be "post-event" data as defined herein, however, the processing of such data would be consistent with the methodology of CPR assessment process 300.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method for assessing cardio-pulmonary resuscitation ("CPR") performed during resuscitation therapy, said method comprising:

receiving post-event data for a patient, said post-event data representing at least one patient signal electronically captured during a resuscitation event;

analyzing characteristics of said post-event data to identify periods during which chest compressions were administered to said patient;

deriving a CPR figure of merit from said post-event data, said CPR figure of merit being indicative of temporal characteristics of CPR administered to said patient, relative to said resuscitation event; and obtaining an event time interval for said resuscitation event, wherein said resuscitation event includes at least one interval of chest compression delivery and at least one interval of defibrillation therapy delivery, and wherein said CPR figure of merit comprises a temporal CPR percentage representing a percentage of said event time interval during which chest compressions were administered to said patient.

2. A method according to claim 1, further comprising analyzing characteristics of said post-event data to identify times during said resuscitation event when defibrillation pulses were administered to said patient, wherein said CPR figure of merit comprises a pre-defibrillation pause indicator that represents a period between a defibrillation pulse and a final chest compression administered to said patient prior to said defibrillation pulse.

3. A method according to claim 1, further comprising analyzing characteristics of said post-event data to identify times during said resuscitation event when defibrillation pulses were administered to said patient, wherein said CPR figure of merit comprises a post-defibrillation pause indicator that represents a period between a defibrillation pulse and an initial chest compression administered to said patient subsequent to said defibrillation pulse.

4. A method according to claim 1, further comprising analyzing characteristics of said post-event data to identify times during said resuscitation event when individual chest compressions were administered to said patient during a CPR cycle, wherein said CPR figure of merit comprises a compression frequency indicator that represents a period between said individual chest compressions.

5. A method according to claim 1, further comprising analyzing characteristics of said post-event data to identify CPR cycles during said resuscitation event, wherein said CPR figure of merit comprises a CPR cycle indicator that represents a period between said CPR cycles.

6. A method according to claim 1, further comprising generating a report containing said CPR figure of merit.

* * * * *